(12) United States Patent
Vondenhoff (10) Patent No.: US 12,385,907 B2
(45) Date of Patent: Aug. 12, 2025

(54) TRANSITION METAL CHELATING BEADS

(71) Applicant: Roche Diagnostics Operations, Inc., Indianapolis, IN (US)

(72) Inventor: Gaston Hubertus Maria Vondenhoff, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 912 days.

(21) Appl. No.: 17/481,965

(22) Filed: Sep. 22, 2021

(65) Prior Publication Data
US 2022/0009963 A1 Jan. 13, 2022

Related U.S. Application Data

(63) Continuation of application No. PCT/EP2020/058718, filed on Mar. 27, 2020.

(30) Foreign Application Priority Data

Mar. 29, 2019 (EP) .................................... 19166197

(51) Int. Cl.
| | |
|---|---|
| G01N 33/543 | (2006.01) |
| A61K 31/16 | (2006.01) |
| B01J 20/22 | (2006.01) |
| C07C 259/00 | (2006.01) |
| C07C 259/04 | (2006.01) |
| G01N 1/34 | (2006.01) |
| G01N 33/68 | (2006.01) |
| G01N 33/92 | (2006.01) |
| C07K 5/068 | (2006.01) |
| C07K 5/09 | (2006.01) |
| C07K 19/00 | (2006.01) |

(52) U.S. Cl.
CPC ....... *G01N 33/54326* (2013.01); *A61K 31/16* (2013.01); *B01J 20/22* (2013.01); *B01J 20/223* (2013.01); *C07C 259/00* (2013.01); *C07C 259/04* (2013.01); *G01N 1/34* (2013.01); *G01N 33/68* (2013.01); *G01N 33/92* (2013.01); *C07K 5/06086* (2013.01); *C07K 5/0815* (2013.01); *C07K 19/00* (2013.01); *Y10S 502/507* (2013.01); *Y10S 930/28* (2013.01)

(58) Field of Classification Search
CPC ............... G01N 33/54326; G01N 1/34; C07K 5/06086; C07K 5/0815; C07K 19/00
See application file for complete search history.

(56) References Cited

U.S. PATENT DOCUMENTS

| | | |
|---|---|---|
| 7,112,552 B2 | 9/2006 | Simpson et al. |
| 7,932,326 B2 * | 4/2011 | Yokel ................... B01J 20/3253 |
| | | 560/12 |
| 2011/0070657 A1 * | 3/2011 | Josephson .......... A61K 49/1863 |
| | | 556/110 |
| 2015/0283536 A1 | 10/2015 | Goerlich et al. |
| 2019/0022103 A1 | 1/2019 | Chevrion et al. |

FOREIGN PATENT DOCUMENTS

| | | |
|---|---|---|
| CN | 104740654 A | 7/2015 |
| JP | 2010535725 A | 8/2008 |
| JP | 2018501312 A | 1/2018 |
| WO | 2009019012 A2 | 2/2009 |
| WO | 2018189286 A1 | 10/2018 |
| WO | WO-2018189287 A1 * | 10/2018 ............ B01J 20/267 |

OTHER PUBLICATIONS

Zhao et al., Journal of Water Process Engineering, 4, 2014, 47-57. Published online Sep. 27, 2014. (Year: 2014).*
Bylda et al., Recent advances in sample preparation techniques to overcome difficulties encountered during quantitative analysis of small molecules from biofluids using LC-MC/MS; Analyst, 2014, vol. 139, 12-pages.
Guérarda et al., Investigation of Zr(IV) and 89Zr(IV) complexation with hydroxamates: Progress towards designing a better chelator than desferrioxamine B for immuno-PET imaging; Chem Commun (Camb), 2013, vol. 49, No. 10, pp. 1002-1004.
Guérarda et al., Rational Design, Synthesis and Evaluation of Tetrahydroxamic Acid Chelators for Stable Complexation of ZrIV; Chemistry, 2014, vol. 20, No. 19, pp. 5584-5591.
(Continued)

*Primary Examiner* — Jane L Stanley
(74) *Attorney, Agent, or Firm* — Taft Stettinius & Hollister LLP (57) ABSTRACT

The present invention relates to a complex comprising a transition metal cation (i); a ligand (ii) comprising at least one chelating group, preferably from 1 to 4 chelating groups, more preferred 2 or 3 chelating groups, wherein the chelating group(s) is/are selected from hydroxamate group —N(O")—C(=O)—R, catechol ate group, carboxyl ate group, partly or totally protonated forms of these chelating groups and mixtures of these chelating groups and/or their partly or totally protonated forms, wherein R is hydrogen or a C1 to C5 alkyl group; and a magnetic bead (iii); wherein the magnetic bead (iii) and the ligand (ii) are covalently bonded. The invention also relates to the use of the complex for reduction of the content of at least one phosphor-oxy-substance, which preferably comprises a structural element —O—P(O")(=O)—O— within its structure, in a fluid sample, as well as to a method for decreasing the content of at least one phosphor-oxy-substance, preferably a phospholipid, in a fluid sample, comprising a step of adding the complex. The invention further relates to a supernatant obtained or obtainable from this method and to the use of a supernatant obtained or obtainable from the method for qualitative and/or quantitative determination of at least one analyte in said supernatant. Furthermore, the invention relates to a method for qualitative and/or quantitative determination of at least one analyte in a fluid sample and to a method for determining the kind and/or amount of at least one phosphor-oxy-substance in a fluid sample.

18 Claims, 5 Drawing Sheets

(56) References Cited

OTHER PUBLICATIONS

Rahman et al., Optical detection and efficient removal of transition metal ions from water using poly(hydroxamic acid) ligand; Sensors and Actuators B: Chemical; 2017, 14-pages.
Tan et al., Fluorescent detection of protein kinase based n zirconium ions-immobilized magnetic nanoparticles; Analytica Chimica Acta; 2013, 6-pages.
Bonnie I. Kruft, et al., Quantum mechanical investigation of aqueous desferrioxamine B metal complexes: Trends in structure, binding, and infrared spectroscopy, Journal of Inorganic Biochemistry, Aug. 31, 2013, 129, 150-161.
HybridSPE®-Phospholipid Solid-Phase Extraction Tube for Separation and concentration of Phospholipids, Sigma-Aldrich Japan K. K., May 2014.
International Search Report, European Patent Office, International Patent Application No. PCT/EP2020/058718, Apr. 21, 2020, 5 pages.
Written Opinion of the International Searching Authority, European Patent Office, International Patent Application No. PCT/EP2020/058718, Apr. 21, 2020, 7 pages.
International Preliminary Report on Patentability, European Patent Office, International Patent Application No. PCT/EP2020/058718, Sep. 28, 2021, 8 pages.

\* cited by examiner

TRANSITION METAL CHELATING BEADS

This application is a continuation application of International Application No. PCT/EP2020/058718 filed Mar. 27, 2020, which claims priority to European Application No. 19166197.4 filed Mar. 29, 2019, the disclosures of which are hereby incorporated by reference in their entirety.

FIELD OF THE INVENTION

The present invention relates to a complex comprising a transition metal cation (i); a ligand (ii) comprising at least one chelating group, wherein the chelating group(s) is/are selected from hydroxamate group —N(O$^-$)—C(=O)—R, catecholate group, carboxylate group, partly or totally protonated forms of these chelating groups and mixtures of these chelating groups and/or their partly or totally protonated forms, wherein R is hydrogen or a C1 to C5 alkyl group; and a magnetic bead (iii); wherein the magnetic bead (iii) and the ligand (ii) are covalently bonded.

The invention also relates to the use of the complex for reduction of the content of at least one phosphor-oxy-substance, which preferably comprises a structural element —O—P(O$^-$) (=O)—O— within its structure, in a fluid sample, as well as to a method for decreasing the content of at least one phosphor-oxy-substance, preferably a phospholipid, in a fluid sample, comprising a step of adding the complex. The invention further relates to a supernatant obtained or obtainable from this method and to the use of a supernatant obtained or obtainable from the method for qualitative and/or quantitative determination of at least one analyte in said supernatant. Furthermore, the invention relates to a method for qualitative and/or quantitative determination of at least one analyte in a fluid sample and to a method for determining the kind and/or amount of at least one phosphor-oxy-substance in a fluid sample.

RELATED ART

Phospholipids (PPLs) are abundant molecules in many human sample materials that may compromise diagnostic assays or have a negative impact on system robustness (See Bylda C., Thiele, R., Kobold, U., Volmer, D. A., *Analyst*, 2014, 139, 2265-2276). Similarly, many phospho-oxy compounds (e.g. substances with phosphodiesters) such as (oli-go)nucleotides or phosphorylated peptides and proteins are common (metabolic) substances that may interfere with analyte quantitation.

S/N increase (S/N: signal to noise ratio) is a direct implication of less interference from substances other than the analyte of interest when measured via LC-MS/MS. Although this technique usually removes large portions of interfering matrixes via LC and subsequently selects for defined MRM transitions, quantitation accuracy and sensitivity is in most cases still compromised.

On the other hand, the same substances that are problematic in the quantitation of certain analytes may be interesting analytes themselves for further quantitation. These either highly polar analytes (nucleotides/phosphorylated peptides) or hydrophobic/amphipatic analytes (phospholipids, PPLs) are difficult candidates to (semi-)selectively separate and purify from (human)sample material.

The removal of phospholipids is addressed by several companies. Zirconium (Zr) is known for its capacity to complex with PPLs and is for that reason also commercially available in different forms. However, to remove PPLs from a sample it is not sufficient to add Zr to that sample. The Zr-complexed PPLs have to be removed subsequently from that mixture. There are several commercialized methods and materials to remove phospholipids from samples e.g. Hybrid SPE™ (Sigma Aldrich), Ostro™ (Waters), Captiva™ ND (Agilent) and Phree™ (Phenomenex). However, all commercial materials use a pass-through method, whereby the sample is loaded onto the respective material and eluted. Although these materials and methods seem to be efficient tools in the cleanup of mainly biological samples, the methods are a) not practical (i.e. difficult to combine with an automized sample preparation workflow and requires substantial amounts of sample (large volume), b) expensive, c) require a lot of time, d) generate a lot of waste material, e) only addresses the removal of phospholipids and not the purification of phospholipids as such, f) focus on phospholipid removal only and not on other substances that may interfere.

Magnetic particles are a great tool for capturing analytes from samples. The magnetic properties are of great importance as they allow easy, fast and cheap automation on diagnostic systems and additionally avoid time-consuming centrifugation and filtration steps. Superparamagnetic materials get more attention as they only show magnetization when an external magnetic field is applied. In the absence of an external magnetic field, magnetization appears to be zero (no "memory effect"). Great varieties of beads are known and are commercially available. However, a bead on which a transition metal is conjugated in such a way that it is still capable of complexing with one or two molecules (such as phospholipids) per conjugated transition metal atom is not known so far.

The technical problem underlying the present invention was therefore the provision of a magnetic bead which enables an automized sample preparation workflow and which overcomes the deficiencies mentioned above.

SUMMARY OF THE INVENTION

The problem is solved by the invention with the features of the independent patent claims. Advantageous developments of the invention, which can be realized individually or in combination, are presented in the dependent claims and/or in the following specification and detailed embodiments.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once, typically will be used only once when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such a way with other optional or non-optional features of the invention.

In a first aspect, the present invention relates to complex comprising
  i) a transition metal cation;
  ii) a ligand comprising at least one chelating group, preferably from 1 to 4 chelating groups, more preferred 2 or 3 chelating groups, wherein the chelating group(s) is/are selected from hydroxamate group —N(O⁻)—C(=O)—R, catecholate group, carboxylate group, partly or totally protonated forms of these chelating groups and mixtures of these chelating groups and/or their partly or totally protonated forms, wherein R is hydrogen or a C1 to C5 alkyl group;
  iii) a magnetic bead;
wherein the magnetic bead (iii) and the ligand (ii) are covalently bonded.

It was found that the inventive complex was usable to remove phosphor-oxy-substances, which preferably comprises a structural element —O—P(O⁻)(=O)—O— within their structure, from sample materials and it use had a positive effect on S/N, i.e. a S/N increase of factor ~2 was achieved when compared to the non-treated sample. This allows for a more sensitive and more accurate quantitation of analytes.

The covalent bond between magnetic bead (iii) and ligand (ii) may be any kind of suitable bond type, for example an amide bond, an amine bond, an ester bond, or a (thio)ether bond. In one embodiment, magnetic bead (iii) and ligand (ii) are covalently bonded by an amide bond. Each chelating group—hydroxamate group, catecholate group, carboxylate group, as well as their respective partly or totally protonated form—has two hetero atoms able to coordinate to a positively charged coordination centrum such as a metal cation. That is, each of these chelating groups has two donor atoms.

According to one embodiment of the complex, the ligand (ii) has the general structure (I)

(I)

wherein:
  --- is the bond to the magnetic bead (iii);
  A is selected from the group consisting of a hydrogen atom, a —X—Y—(CH$_2$)$_m$—CH$_2$—(CHR$^3$)$_q$—R$^2$- group and R$^3$;

n, m are independently zero or an integer from 1 to 5;
p, q are independently an integer from 1 to 10, preferably an integer from 3 to 5, more preferred 3 or 4;
X is CH$_2$— or NH—;
Y is CH$_2$— or —C(=O)—;
R$^1$, R$^2$ are independently selected from the group consisting of hydroxamate group N(O⁻)—C(=O)—R, wherein R is hydrogen or a C1 to C5 alkyl group, catecholate group, carboxylate group and partly or totally protonated forms of these chelating groups;
R$^3$ is a hydrogen atom or a —NHZ group, wherein Z is a protective group, preferably a —C(=O)—O—CH$_2$—C$_6$H$_5$ group (benzyloxycarbonyl group, Cbz) or a tert-butyloxycarbonyl group (Boc).

In one embodiment of the complex, the ligand (ii) has the general structure (Ia):

(Ia)

wherein --- and A have the same meaning as disclosed above with respect to general structure (I).

According to a preferred embodiment of the complex, the ligand (ii) has the general structure (Ia1) or (Ia2):

(Ia1)

(Ia2)

wherein --- and Z have the same meaning as disclosed above with respect to general structure (I).

In one embodiment of the complex, the transition metal cation (i) is selected from the group of platinum-, ruthenium-, iridium-, scandium-, titanium-, vanadium-, chromium-, manganese-, iron-, cobalt-, nickel-, copper- and zinc-cation, more preferably from $Fe^{2+}$, $Fe^{2+}$ and $Zr^{4+}$ and is more preferably $Zr^{4+}$.

The transition-metal-complexing ligand of general structure (I), (Ia), (Ia1) or (Ia2) is bound to beads and forms bi-, quadro- or hexadentate complexes with the transition metal cation (i). For example, hydroxamates are suitable ligands and when three hydroxamate groups are placed in close proximity to transition metal cation (i) such as $Zr^{4+}$, a good hexadentate Zr-complex is formed. In one embodiment of the complex, free coordinative places of the transition metal are occupied by solvent molecules, preferably water. $Zr^{4+}$ tends to form octa-coordinated complexes. (see Guerard F., Lee Y. S., Tripier R., Szajek L. P., Deschamps J. R., Brechbiel M. W., Chem Commun. 2013, 49:1002-1004; Guérard, F.; Lee, Y. S.; Brechbiel, M. W. Chemistry. 2014, 20(19): 5584-5591). Thus, the presence of 2 or three chelating groups, such as hydroxamate groups each having two donor atoms, results in four or two free coordinative places at the $Zr^{4+}$ cation, where ligands of interest, i.e. phosphoroxy-substances, which preferably comprises a structural element —O—P(O⁻)(=O)—O— within their structure, such as PPLs, can be bound, i.e. an exchange of water by the phosphor-oxy-substance, such as PPL, can take place.

In one embodiment of the complex, the magnetic bead (iii) comprises a polymer matrix (P), at least one magnetic particle (M) and at least one $(CH_2)_r$—NH--- group covalently bonded on the polymer matrix (P) surface (S), wherein --- is the bond to the ligand (ii), and r is zero or an integer in the range of from 1 to 10, preferably an integer in the range of from 1 to 5, more preferred in the range of 2 to 4, more preferred 3; wherein the polymer matrix (P) comprises at least one crosslinked (co-)polymer.

The Magnetic Bead (iii)

The magnetic bead (iii) according to the invention have a particle size in the range of from 1 to 60 micrometers, as determined according to ISO 13320.

The magnetic bead (iii) may, in principle, display any geometrical form, however, preferably, the particle is substantially spherical. As used herein, the term "substantially spherical" refers to particles with rounded shapes that are preferably non-faceted or substantially free of sharp corners. In certain embodiments, the substantially spherical particles typically have an average aspect ratio of less than 3:1 or 2:1, for example, an aspect ratio less than 1.5:1, or less than 1.2:1. In a certain embodiment, substantially spherical particles may have an aspect ratio of about 1:1. The aspect ratio ($A_R$) is defined as being a function of the largest diameter ($d_{max}$) and the smallest diameter ($d_{min}$) orthogonal to it ($A_R = d_{min}/d_{max}$). The diameters are determined via SEM or light microscope measurements.

The Polymer Matrix (P)

As described above, the magnetic bead (iii) comprises a polymer matrix (P).

In one embodiment of the complex, the polymer matrix (P) comprises a co-polymer obtained or obtainable by a method comprising polymerization of at least two different monomeric building blocks selected from the group consisting of styrene, functionalized styrenes, vinylbenzylchloride, divinylbenzene, vinylacetate, methylmethaacrylate and acrylic acid, preferably at least two different monomeric building blocks selected from the group consisting of the following monomers:

wherein:
r is zero or an integer in the range of from 1 to 10, preferably an integer in the range of from 1 to 5, more preferred in the range of from 2 to 4, more preferred 3;
$R^1$, $R^2$, $R^3$, $R^4$ and $R^5$ are independently of each other selected from the group consisting of —$N_3$, —$NH_2$, —Br, —I, —F, —NR'R", —NR'R"R'", —COOH, —CN, —OH, —OR', —COOR', —$NO_2$, —$SH_2$, —$SO_2$, —R'(OH)x, —R'(COOH)x, —R'(COOR")x, —R'(OR")x, —R'($NH_2$)x, —R'(NHR")x, —R' (NR"R'")x, —R'(Cl)x, —R' (I)x, —R' (Br)x, —R' (F)x, R'(CN)x, —R'($N_3$)x, —R' ($NO_2$)x, —R'($SH_2$)x, —R' ($SO_2$)x, alkyl, aryl, cycloalkyl, heteroaryl, heterocycloalkyl; with R', R" and R'" being, independently of each other, selected from the group consisting of alkyl, aryl, cycloalkyl, heteroaryl, heterocycloalkyl, halides, hydrogen, sulfides, nitrates and amines; and wherein x is an integer in the range of from 1 to 3.

In one embodiment of the complex, the (co-)polymer of the polymer matrix (P) is crosslinked, wherein the crosslinked (co-)polymer of the polymer matrix (P) is obtained or obtainable by co-polymerizing at least two different monomeric building blocks according to the embodiment above in the presence of at least one monomeric building block which is a crosslinking agent, wherein the crosslinking agent is preferably selected from the group consisting of divinylbenzene, bis(vinylphenyl)ethane, bis(vinylbenzyloxy)hexane, bis(vinylbenzyloxy)dodecane and mixtures of two or more of these crosslinking agents, preferably, the crosslinking agent at least comprises divinylbenzene.

The Magnetic Particle (M)

As described above, the magnetic bead (iii) according to the invention comprise at least one magnetic particle (M).

In one embodiment of the complex, the at least one magnetic particle (M) comprises a compound selected from the group consisting of metal, metal carbide, metal nitride, metal sulfide, metal phosphide, metal oxide, metal chelate and a mixture of two or more thereof.

It is to be understood that each magnetic particle (M) may comprise a mixture of two or more of the above-mentioned group, i.e. two or more of a metal, metal carbide, metal nitride, metal sulfide, metal phosphide, metal oxide, a metal chelate and a mixture of two or more thereof. Further, mixtures of two or more different metals, two or more different metal oxides, two or more different metal carbides, two or more different metal nitrides, two or more different metal sulphides, two or more different metal phosphides, two or more different metal chelates are conceivable. Further, it is to be understood that in case the magnetic bead (iii) according to the invention comprises more than one magnetic particle (M), each of the magnetic particles (M) present in a single magnetic bead (iii) may be the same or may differ from each other. Preferably, all magnetic particles (M) comprised in one magnetic particle are the same. More preferably, the at least one magnetic particle (M) comprises a metal oxide or a metal carbide.

Thus, in one embodiment of the complex, the at least one magnetic particle (M) comprises a metal oxide or a metal carbide, more preferably, an iron oxide, in particular an iron oxide selected from the group consisting of $Fe_3O_4$, $\alpha$-$Fe_2O_3$, $\gamma$-$Fe_2O_3$, $MnFe_xO_y$, $CoFe_xO_y$, $Ni$—$Fe_xO_y$, $CuFe_xO_y$, $ZnFe_xO_yCdFe_xO_y$, $BaFe_xO$ and $SrFe_xO$, wherein x and y vary depending on the method of synthesis, and wherein x is preferably an integer of from 1 to 3, more preferably 2, and wherein y is preferably 3 or 4 most preferably, $Fe_3O_4$.

In one preferred embodiment of the complex, the magnetic particle and thus the magnetic bead (iii) is superparamagnetic. The term "superparamagnetic" is known to the person skilled in the art and refers to the magnetic property encountered in particular for particles smaller than a single magnetic mono-domain. Such particles steadily orient upon applying an external magnetic field until a maximum value of the global magnetization, dubbed saturation magnetization, is reached. They relax when removing the magnetic field, with no magnetic hysteresis (no remanence) at room temperature. In the absence of an external magnetic field, superparamagnetic particles exhibit a non-permanent magnetic moment due to thermal fluctuations of the dipole orientation (Neel relaxation) and particle position (Brownian relaxation).

The magnetic particles (M) are present in the center of the magnetic bead forming one or more so called "core(s)" or are evenly distributed in pores throughout the magnetic beads (iii), i.e. substantially evenly distributed within the polymer matrix (P).

The magnetic particles (M) preferably comprise, more preferably consist of nanoparticles. The nanoparticles are preferably the part which displays the magnetism, preferably super-paramagnetism of a particle. Nanoparticles are sometimes also referred to as "magnetic nanoparticles" herein.

As used herein, the term "nanoparticle" refers to a particle being less than 100 nanometers in at least one dimension, i.e. having a diameter of less than 100 nm. Preferably, the nanoparticle according to the invention has a diameter in the range of from 1 to 20 nm, preferably 4 to 15 nm, as determined according to TEM-measurements.

Each nanoparticle has a diameter in the range of from 1 to 20 nm, preferably 4 to 15 nm, as determined according to TEM-measurements. Preferably, the at least one magnetic nanoparticle is superparamagnetic.

The magnetic particle (M) may comprise only one nanoparticle or more than one nanoparticle. In one embodiment, it comprises from 1 to 20 nanoparticles. In another embodiment, it comprises more than 20 nanoparticles, preferably 100 to 1.5 million nanoparticles, more preferably 750-750,000 nanoparticles, more preferably 1,750-320,000 nanoparticles, in particular 90,000-320,000 nanoparticles. The nanoparticles may be present as individual (i.e. separate) particles, for example, the individual nanoparticles may be evenly distributed in pores throughout the magnetic beads, or they may form aggregates consisting of several nanoparticles. Theses aggregates may have different sizes depending on the number of included nanoparticles. In one embodiment, so called supraparticles are formed. According to this embodiment, the magnetic particle (M) comprises more than 20 nanoparticles, and, typically more than 100 nanoparticles, wherein these nanoparticles are preferably aggregated with each other to form a supraparticle. More preferably, in this case, the magnetic particle (M) comprises a supraparticle consisting of aggregated nanoparticles. Preferably, in this case, the magnetic particle (M) comprises a supraparticle which comprises between 100 to 1.5 million nanoparticles more preferably 750-750,000 nanoparticles, more preferably 1,750-320,000 nanoparticles, in particular 90,000-320,000 nanoparticles. In a preferred embodiment, where a supraparticle is present, the magnetic particle (M) comprising the supraparticle is present in the center of the magnetic bead and forms a so called "core". Preferably, such a core formed by magnetic particles (M) has a diameter in the range of from 80 to 500 nm, more preferably 150 to 400 nm, and most preferably 200 to 300 nm, as determined according to DLS (ISO 22412).

Preferably the amount of magnetic particles (M) is chosen so that a desired saturation magnetization saturation of the magnetic bead (iii) is achieved. Preferably, the magnetic bead (iii) according to the invention has a saturation magnetization of at least 1 A $m^2$/kg. Preferably, the saturation magnetization is at least 1 A $m^2$/kg, more preferably at least 2 A $m^2$/kg, more preferably at least 3 A $m^2$/kg, more preferably at least 4 A $m^2$/kg, more preferably at least 5 A $m^2$/kg, more preferably at least 6 A $m^2$/kg, more preferably at least 7 A $m^2$/kg, more preferably at least 8 A $m^2$/kg, more preferably at least 9 A $m^2$/kg, and in particular at least 10 A $m^2$/kg, such as in the range of from 10 A $m^2$/kg to 20 A $m^2$/kg, more preferably in the range of from 10 A $m^2$/kg to 30 A $m^2$/kg, as determined according to ASTM A 894/A 894M.

Use of the Complex

The invention further relates to the use of complex as described above for decreasing the content of at least one phosphor-oxy-substance, which preferably comprises a structural element O—P(O$^-$)(=O)—O— within its structure, in a fluid sample. Preferably, the at least one phosphor-oxy-substance is selected from the group consisting of phospholipid, phosphodiester, oligonucleotide, polynucleotide, phosphorylated peptide and phosphorylated protein, preferably a phospholipid.

Method for Decreasing the Content of at Least One Phosphor-Oxy-Substance

The invention further relates to a method for decreasing the content of at least one phosphoroxy-substance, preferably a phospholipid, in a fluid sample, comprising the steps:
  a) providing a fluid sample comprising at least one analyte of interest and at least one phosphor-oxy-substance;
  b) optionally adjusting the pH value of the fluid sample, so that the pH value of the fluid sample is in the range of from 2.5 to 12 thereby obtaining a pH adjusted fluid sample;

c) adding at least one first complex, preferably in suspension, more preferred in aqueous suspension, wherein the complex comprises:
  i) a transition metal cation;
  ii) a ligand comprising at least one chelating group, preferably from 1 to 4 chelating groups, more preferred 2 or 3 chelating groups, wherein the chelating group(s) is/are selected from hydroxamate group —N(O⁻)—C(=O)—R, catecholate group, carboxylate group, partly or totally protonated forms of these chelating groups and mixtures of these chelating groups and/or their partly or totally protonated forms, wherein R is hydrogen or a C1 to C5 alkyl group;
  iii) a magnetic bead;
  wherein the magnetic bead (iii) and the ligand (ii) are covalently bonded; thereby forming a suspension comprising a second complex, which comprises the first complex and the at least one phosphor-oxy-substance in complexed form;
d) spacely separating the second complex in the suspension obtained in (c) by application of a magnetic field, thereby obtaining a supernatant substantially free of the second complex;
e) removing the supernatant, thereby obtaining a separated second complex.

The concentration of the at least one first complex in suspension, more preferred in aqueous suspension, is preferably in the range of from 10 to 150 mg/ml, more preferred in the range of from 25 to 75 mg/ml (50+/−25 mg/ml).

In one embodiment, the method for decreasing the content of at least one phosphor-oxy-substance further comprises:
  f) applying a washing solution to the separated second complex followed by spacely separation of the second complex by magnetic field and removal of the remaining supernatant, thereby obtaining a further supernatant and a further separated second complex.

In one embodiment, the method for decreasing the content of at least one phosphor-oxy-substance further comprises:
  g) fusion of the supernatants from (e) and (f).

The present invention also relates to a supernatant obtained or obtainable from the method as described above in the section "method for decreasing the content of at least one phosphor-oxy-sub stance".

The present invention also relates to the use of a supernatant obtained or obtainable from the method as described above for qualitative and/or quantitative determination of at least one analyte in said supernatant.

The present invention also relates to a method for qualitative and/or quantitative determination of at least one analyte in a fluid sample, comprising the steps of the decreasing-method as described above and further comprising a step of qualitative and/or quantitative determination of the at least one analyte in the supernatant obtained from (e) and/or (f) and/or (g).

The present invention further relates to a method for determining the kind and/or amount of at least one phosphor-oxy-substance in a fluid sample, comprising the steps of the decreasing method as described above and further comprising:
  h) adding an aqueous and/or organic elution solution to the (further) separated second complex obtained according to (e) and/or (f), wherein the aqueous and/or organic elution solution contains a buffer, an acid and/or a reductant, and/or wherein the adding is done in a reductive atmosphere, thereby separating the at least one phosphor-oxy-substance from the separated second complex and obtaining a solution comprising the at least one phosphor-oxy-substance;
  j) determining the kind and/or amount of the at least one phosphor-oxy-substance in the solution obtained according to (h).

According to one embodiment, at least a buffer is contained in the aqueous and/or organic elution solution, which results in a pH change. The change in pH may cause the release of the phosphor-oxy substance from the magnetic bead. The mechanism is simply the protonation of the chelating moiety whereby the complex is disrupted, causing the release. A buffer means a system comprising an organic acid and its related anion, wherein the system is capable of pH buffering. According to another embodiment, the aqueous and/or organic elution solution contains at least one acid. There are almost no restrictions regarding the at least one acid as long as it does not interfere with later measurement. In one embodiment, the at least one acid is selected from the group of volatile organic acids, wherein volatile organic acid comprises all carboxylic acids having a boiling point at normal pressure (1013 mbar) below 200° C., preferably below 150° C., preferably from the group consisting of formic acid, acetic acid and mixtures of formic and acetic acid. Non-volatile inorganic acids such as HCl and phosphoric acid are excluded. The change in pH causes the release of the phosphor-oxy substance from the magnetic bead. The mechanism is simply the protonation of the chelating moiety thereby the complex is disrupted, causing the release. Another method that may cause the release of the phosphor-compound is by reduction of the metal. This also leads to disruption of the complex. Thus, according to one embodiment, the aqueous and/or organic elution solution contains at least one reductant, which causes the release of the phosphor-compound by reduction of the metal. This also results in disruption of the complex. The at least one reductant is in one embodiment selected from the group of organic reductants, wherein the organic reductant is preferably selected from the group consisting of dithiothreitol, dithioerythritol, mecaptoethanol and mixtures of these reductants.

According to one embodiment, adding of the aqueous and/or organic elution solution is done in a reductive atmosphere or the aqueous and/or organic elution solution comprising the second complex is exposed to a reductive atmosphere, for example a hydrogen atmosphere, whereby the phosphor-compound is also released, i.e. the complex is disrupted.

According to one embodiment, the methods for disruption of the complex are mixed in that the aqueous and/or organic elution solution contains a least one agent select from the group of a buffer, an acid, a reductant and mixtures of two or more of these agents, and/or wherein the adding of the aqueous and/or organic elution solution according to (h) is done in a reductive atmosphere.

The present invention is further illustrated by the following embodiments and combinations of embodiments as indicated by the respective dependencies and back-references. In particular, it is noted that in each instance where a range of embodiments is mentioned, for example in the context of a term such as "The . . . of any of embodiments 1 to 4", every embodiment in this range is meant to be explicitly disclosed for the skilled person, i.e. the wording of this term is to be understood by the skilled person as being synonymous to "The . . . of any of embodiments 1, 2, 3, and 4".

1. A complex comprising
   i) a transition metal cation;
   ii) a ligand comprising at least one chelating group, preferably from 1 to 4 chelating groups, more preferred 2 or 3 chelating groups, wherein the chelating group(s) is/are selected from hydroxamate group —N(O⁻)—C(=O)—R, catecholate group, carboxylate group, partly or totally protonated forms of these chelating groups and mixtures of these chelating groups and/or their partly or totally protonated forms, wherein R is hydrogen or a C1 to C5 alkyl group;
   iii) a magnetic bead;
   wherein the magnetic bead (iii) and the ligand (ii) are covalently bonded.
2. The complex of embodiment 1, wherein the ligand (ii) has the general structure (I)

wherein:
   --- is the bond to the magnetic bead (iii);
   A is selected from the group consisting of a hydrogen atom, a —X—Y—(CH$_2$)$_m$—CH$_2$—(CHR$^3$)$_q$—R$^2$-group and R$^3$;
   n, m are independently zero or an integer from 1 to 5;
   p, q are independently an integer from 1 to 10, preferably an integer from 3 to 5, more preferred 3 or 4;
   X is CH$_2$— or NH—;
   Y is CH$_2$— or —C(=O)—;
   R$^1$, R$^2$ are independently selected from the group consisting of hydroxamate group —N(O⁻)—C(=O)—R, wherein R is hydrogen or a C1 to C5 alkyl group, catecholate group, carboxylate group and partly or totally protonated forms of these chelating groups;
   R$^3$ is a hydrogen atom or a NHZ group, wherein Z is a protective group, preferably a —C(=O)—O—CH$_2$—C$_6$H$_5$ group (benzyloxycarbonyl group, Cbz) or a tert-Butyloxycarbonyl group (Boc).
3. The complex according to embodiment 1 or 2, wherein the ligand (ii) has the general structure (Ia):

wherein --- and A have the same meaning as in embodiment 2.

4. The complex according to any one of embodiments 1 to 3, wherein the ligand (ii) has the general structure (Ia1) or (Ia2):

wherein --- and Z have the same meaning as in embodiment 2.

5. The complex according to any one of embodiments 1 to 4, wherein the transition metal cation (i) is selected from the group of platinum-, ruthenium-, iridium-, scandium-, titanium-, vanadium-, chromium-, manganese-, iron-, cobalt-, nickel-, copper- and zinc-cation, more preferably from Fe$^{2+}$, Fe$^{2+}$ and Zr$^{4+}$ and is more preferably Zr$^{4+}$.
6. The complex according to any one of embodiments 1 to 5, wherein free coordinative places of the transition metal are occupied by solvent molecules, preferably water.
7. The complex according to any one of embodiments 1 to 6, wherein the magnetic bead (iii) comprises a polymer matrix (P), at least one magnetic particle (M) and at least one (CH$_2$)$_r$—NH--- group covalently bonded on the polymer matrix (P) surface (S), wherein --- is the bond to the ligand (ii), and r is zero or an integer in the range of from 1 to 10, preferably an integer in the range of from 1 to 5, more preferred in the range of from 2 to 4, more preferred 3; wherein the polymer matrix (P) comprises at least one crosslinked (co-)polymer.
8. The complex according to embodiment 7, wherein the polymer matrix (P) comprises a co-polymer obtained or obtainable by a method comprising polymerization of at least two different monomeric building blocks selected from the group consisting of styrene, functionalized styrenes, vinylbenzylchloride, divinylbenzene, vinylacetate, methylmethaacrylate and acrylic acid, preferably at least two different monomeric building blocks selected from the group consisting of the following monomers:

wherein r is zero or an integer in the range of from 1 to 10, preferably an integer in the range of from 1 to 5, more preferred in the range of from 2 to 4, more preferred 3; $R^1$, $R^2$, $R^3$, $R^4$ and $R^5$, being independently of each other selected from the group consisting of —$N_3$, —$NH_2$, —Br, —I, —F, —NR'R", —NR'R"R' ", —COOH, —CN, —OH, —OR', —COOR', —$NO_2$, —$SH_2$, —$SO_2$, —R'(OH)x, —R'(COOH)x, —R'(COOR' ')x, —R' (OR' ')x, —R'($NH_2$)x, —R'(NHR")x, —R'(NR"R''')x, —R'(Cl)x, —R' (I)x, —R' (Br)x, —R' (F)x, R'(CN)x, —R'($N_3$)x, —R'($NO_2$)x, —R'($SH_2$)x, —R'($SO_2$)x, alkyl, aryl, cycloalkyl, heteroaryl, heterocycloalkyl; with R', R" and R''' being, independently of each other, selected from the group consisting of alkyl, aryl, cycloalkyl, heteroaryl, heterocycloalkyl, halides, hydrogen, sulfides, nitrates and amines; and wherein x is an integer in the range of from 1 to 3.

9. The complex according to embodiment 7 or 8, wherein the (co-)polymer of the polymer matrix (P) is crosslinked, wherein the crosslinked (co-)polymer of the polymer matrix (P) is obtained or obtainable by co-polymerizing at least two different monomeric building blocks according to embodiment 8 in the presence of at least one monomeric building block which is a crosslinking agent, wherein the crosslinking agent is preferably selected from the group consisting of divinylbenzene, bis(vinylphenyl)ethane, bis(vinylbenzyloxy)hexane, bis(vinylbenzyloxy)dodecane and mixtures of two or more of these crosslinking agents, preferably, the crosslinking agent at least comprises divinylbenzene.

10. The complex according to any of embodiments 7 to 9, wherein the at least one magnetic particle (M) comprises a compound selected from the group consisting of metal, metal carbide, metal nitride, metal sulfide, metal phosphide, metal oxide, metal chelate and a mixture of two or more thereof 11. The complex according to any one of embodiments 7 to 10, wherein the at least one magnetic particle (M) comprises a metal oxide or a metal carbide, more preferably, an iron oxide, in particular an iron oxide selected from the group consisting of $Fe_3O_4$, α-$Fe_2O_3$, γ-$Fe_2O_3$, $MnFe_xO_y$, $CoFe_xO_y$, $NiFe_xO_y$, $CuFe_xO_y$, $ZnFe_xO_y$, $CdFe_xO_y$, $BaFe_xO$ and $SrFe_xO$, wherein x and y vary depending on the method of synthesis, and wherein x is preferably an integer of from 1 to 3, more preferably 2, and wherein y is preferably 3 or 4 most preferably, $Fe_3O_4$.

12. The complex according to any one of embodiments 1 to 11, wherein the magnetic particle is superparamagnetic.

13. Use of complex according to any one of embodiments 1 to 12 for decreasing the content of at least one phosphor-oxy-substance, which preferably comprises a structural element —O—P(O⁻)(=O)—O— within its structure, in a fluid sample.

14. The use according to embodiment 13, wherein the at least one phosphor-oxy-substance is selected from the group consisting of phospholipid, phosphodiester, oligonucleotide, polynucleotide, phosphorylated peptide and phosphorylated protein, preferably a phospholipid.

14. A method for decreasing the content of at least one phosphor-oxy-substance, preferably a phospholipid, in a fluid sample, comprising the steps:
 a) providing a fluid sample comprising at least one analyte of interest and at least one phosphor-oxy-substance;
 b) optionally adjusting the pH value of the fluid sample, so that the pH value of the fluid sample is in the range of from 2.5 to 12 thereby obtaining a pH adjusted fluid sample;
 c) adding at least one first complex, preferably in suspension, more preferred in aqueous suspension, wherein the complex comprises:
  i) a transition metal cation;
  ii) a ligand comprising at least one chelating group, preferably from 1 to 4 chelating groups, more preferred 2 or 3 chelating groups, wherein the chelating group(s) is/are selected from hydroxamate group —N(O⁻)—C(=O)—R, catecholate group, carboxylate group, partly or totally protonated forms of these chelating groups and mixtures of these chelating groups and/or their partly or totally protonated forms, wherein R is hydrogen or a C1 to C5 alkyl group;
  iii) a magnetic bead;
  wherein the magnetic bead (iii) and the ligand (ii) are covalently bonded; thereby forming a suspension comprising a second complex, which comprises the first complex and the at least one phosphor-oxy-substance in complexed form;
 d) spacely separating the second complex in the suspension obtained in (c) by application of a magnetic field, thereby obtaining a supernatant substantially free of the second complex;
 e) removing the supernatant, thereby obtaining a separated second complex.

16. The method for decreasing the content of at least one phosphor-oxy-substance according to embodiment 15 further comprising:
 f) applying a washing solution to the separated second complex followed by spacely separation of the second complex by magnetic field and removal of the remaining supernatant, thereby obtaining a further supernatant and a further separated second complex.

17. The method according to embodiment 16 further comprising:
    g) fusion of the supernatants from (e) and (f).
18. A supernatant obtained or obtainable from the method of any one of embodiments 15 to 17.
19. Use of a supernatant obtained or obtainable from the method of any one of embodiments 15 to 18 for qualitative and/or quantitative determination of at least one analyte in said supernatant.
20. A method for qualitative and/or quantitative determination of at least one analyte in a fluid sample, comprising the steps of the purification method according to any one of embodiments 15 to 17 and further comprising a step of qualitative and/or quantitative determination of the at least one analyte in the supernatant obtained from (e) and/or (f) and/or (g).
21. A method for determining the kind and/or amount of at least one phosphor-oxy-substance in a fluid sample, comprising the steps of the purification method according to any one of embodiments 15 to 17 and further comprising:
    h) adding an aqueous and/or organic elution solution to the (further) separated second complex obtained according to (e) and/or (f), wherein the aqueous and/or organic elution solution contains an acid, a buffer and/or a reductant, and/or wherein the adding is done in a reductive atmosphere, thereby separating the at least one phosphor-oxy-substance from the separated second complex and obtaining a solution comprising the at least one phosphor-oxy-substance;
    j) determining the kind and/or amount of the at least one phosphor-oxy-substance in the solution obtained according to (h).

EXAMPLES

1. Chemicals

| Abbreviation | Chemical name |
| --- | --- |
| magnetic bead 1 | superparamagnetic beads ($Fe_3O_4$) with crosslinked polystyrene matrix having primary amino groups on the outer surface (propyl amino groups) |
| DMF | N,N-Dimethylformamide |
| Ligand 1 -diacetylated form | benzyl ((8S,11S)-4,15-diacetyl-8-(ethylcarbamoyl)-2,10,17-tri-oxo-3,16-dioxa-4,9,15-triazaoctadecan-11-yl)carbamate |
| HOBt | 1-Hydroxybenzotriazole |
| DIC | Diisopropylcarbodiimide |
| — | N-methylpiperidine |
| MeOH | methanol |
| $ZrCl_4$ | Zirconium (IV) tetrachloride |
| DIPEA | N,N-Diisopropylethylamine |
| $K_3PO_4/K_2HPO_4$ | Tri potassium phosphate/di potassium hydrogen phosphate |
| HCOOH | Formic acid |
| mCPBA | m-chloroperoxybenzoic acid |

2. Experimental Design

Zr-complexed magnetic beads that remove residual matrix, i.e. impurities, from semi-cleaned up Human serum were synthesized and subsequently evaluated for their propensity to i) yield increase in signal to noise ratio (S/N) of analytes that are quantified using LCMS/MS methods and ii) remove lysophosphatidylcholine, an important phospholipid.

S/N increase is a direct implication of less interference from substances other than the analyte of interest when measured via LC-MS/MS. Although this technique usually removes large portions of interfering matrixes via LC and subsequently selects for defined MRM transitions, quantitation accuracy and sensitivity is in most cases still compromised. Hence, a cleaner sample allows for less ion suppression, and thereby allowing for a higher sensitivity and a higher accuracy. Indeed, the implications of a clean sample on system robustness are numerous. One direct measurable parameter that is known to compromise the longevity of an accurate and sensitive measuring LC-MS/MS system are phospholipids. To this end, one lysophosphatidylcholine (18:0) (LPC 18:0) was chosen as a representative substance that was quantified to evaluate if the new beads would be capable of removing this substance.

2.1 Conjugation of Zirconium Chelating Ligands to Magnetic Beads and Chelation with Zr As suitable bead, magnetic bead 1 having free amino groups were selected. To the free amine, ligand 1 in its diacetylated form, i.e. a dipeptide of O-Acetyl hydroxamate derivatized ornithine, was coupled using standard peptide chemistry. Subsequently, the hydroxy groups were deprotected and the ligands were complexed with Zr (see Scheme 2) thereby obtaining Zr-complexed magnetic beads.

Scheme 1

17
-continued

Conjugation of ligand 1 in its diacetylated from to the magnetic bead resulting in a hydroxamate bead, Deprotection of the hydroxamate groups of ligand 1, and complexation with Zr(IV) resulting in a Zr-complexed magnetic bead.

2.2 Evaluation of Zr-Complexed Magnetic Beads for their Capacity to Remove Phospholipids and Improve Signal to Noise Ratio (S/N) in LC-MS/MS Quantitation.

The use of the Zr-complexed magnetic beads was to remove as many substances as possible from (semi-clean) biological matrices. The goal of this experiment was to show that these beads are capable of removing important matrix components and thereby improve i) the quantitation (i.e. S/N) of clinically relevant analytes and ii) system robustness (less residual matrix obviously adds to the longevity of the LC-MS/MS system as a whole).

To this end two experiments were carried out. The first experiment was related to examining the S/N from cleaned up serum and the second was related to measuring lysophosphatidylcholine 18:0 (LPC 18:0).

Figure 1:
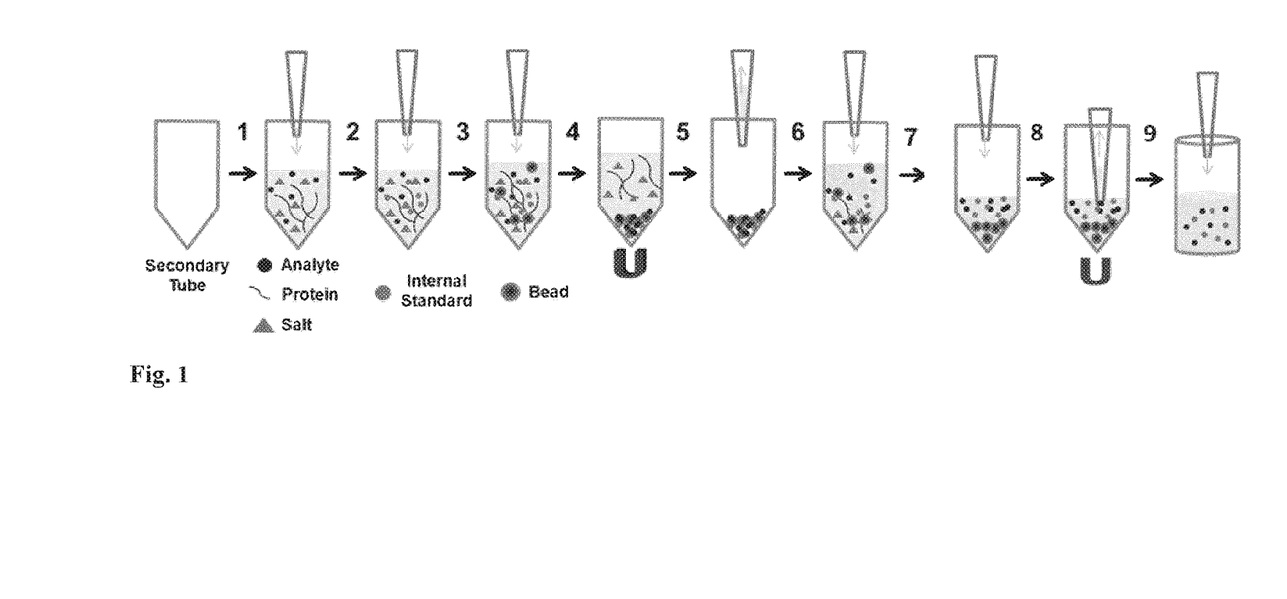
FIG. 1: shows the steps of workup of spiked serum prior to final purification with Zr-complexed magnetic beads.

To obtain sufficient sample that contains clinically relevant analytes that were cleaned up from serum using an enrichment workflow that was found to yield high recoveries of these analytes, 100 μl portions of spiked serum were worked up 5 times, yielding 300 μl of semi-clean eluate, according to the method described below (see also FIG. 1). This eluate was then diluted once more with water (1:1). These mixtures were next aliquoted in 9 vessels. To vessels 1-3 15 μl water was charged, to vessels 4-6 15 μl magnetic bead 1 were charged and to vessels 7-9 Zr-complexed magnetic beads were charged. The tubes were next shortly vortexed and left to stand for 5 min. Subsequently, the supernatant was transferred to a HPLC vial. The samples were next measured via LC-MS/MS to determine SN for relevant analytes and to compare LPC (18:0) contents from these samples.

18

3. Examples

Reference Example 1 Synthesis of Ligand 1 and its Diacetylated Form Respectively (a Dipeptide of O-Acetyl Hydroxamate Derivatized Ornithine)

Scheme 2

Synthesis of ligand 1 in its diacetylated from
To a benzyloxycarbonyl (Cbz) protected dipeptide of ornithine, benzylaldehye was added to form an imine. The resulting product was next oxidized using mCPBA, followed by a hydrolyzation and a subsequent acetylation. The resulting product—ligand 1 in its diacetylated form—can be used as such to be coupled to the free amine of an appropriate bead via its free carboxylic acid, using standard peptide chemistry.

Example 1—Synthesis of a Magnetic Beads, Bonded Via an Amide Bond to a Dipeptide of O-Acetyl Hydroxamate Derivatized Ornithine (Hydroxamate Beads)

To 30 mg magnetic beads 1 about 9 μmol ligand here 1 in its diacetylated form—may be coupled, assuming an molecular weight of 1 kDa. Based on this protocol, to 30 mg of magnetic beads 1, DMF (0.25 ml) was added and stirred. Hereto, ligand 1 in its diacetylated form (20.8 mg, 4 eq. 36 μmop, HOBt (5 mg, 2 eq., 18 μmop, DIC (5.6 μl, eq. 36 μmol), N-methylpiperidine (4.3 μl, 2 eq., 18 μmop in DMF (0.25 ml) was added and the flasks gently mixed by rolling for 2 h at room temperature.

Following this amide conjugation, the reaction mixture was removed from the conjugated beads (magnetic beads 1 coupled by amide bond with ligand 1) by applying a magnetic field. The conjugated beads were washed 3 times with MeOH and 3 times with water and twice more with MeOH. The solvent was then removed and the conjugated beads resuspended in 6% N-methylpiperidine in MeOH. Again, the conjugated beads were washed 3 times with MeOH and 3 times with water. Next, the solvent was removed, and the conjugated beads dried under vacuo, yielding 30 mg of conjugated beads.

The used reaction mixture (0.5 ml) that was removed from the beads after reaction was assessed for its presence of unreacted dipeptide: 6% DIPEA in MeOH (1 ml) was added and left to stand for 30 min. To this, $FeCl_3$ was added, giving it a yellow color.

A reaction mixture that was not brought into contact with free-amine beads, i.e. magnetic beads 1, served as a negative control. This reaction mixture underwent the same treatment (i.e. 6% DIPEA in MeOH was added, mixture left to stand for 30 min. and subsequent addition of $FeCl_3$). The color of this mixture was dark brown. This indicated that most, if not all dipeptide that was brought into reaction with the free-amine bead had reacted. Namely, any non-reacted dipeptide would complex with $Fe^{3+}$ and give a brown color, as is the case for the negative control.

Example 2—Synthesis of a Zirconium Complex of the Beads from Example 1 (Zr-Complexed Magnetic Beads)

Hydroxamate beads (30 mg) were suspended in water (1 ml) and reacted with $ZrOCl_2$ (250 μl, 1 M in water) by rolling at room temperature for 2 h. The reaction mixture was removed from the conjugated beads by applying a magnetic field. The conjugated beads were then washed 3 times with water. Beads were then resuspended in 1 ml of water, yielding 30 mg/ml Zr-complexed magnetic beads.

Example 3—Workup of Spiked Serum and Final Purification with Zr-Complexed Magnetic Beads A standard bead-assessment workflow was as follows (see FIG. 1): In the tube, sample to which analytes of interest have been spiked (see Table 1 for details) was charged (step 1). The analytes used were aldosterone, benzoylecgonine and nortriptyline. Next a pH adjustment reagent was added that set the pH of the mixture (step 2). To this, a bead suspension of the Zr-complexed magnetic beads from Example 2 was added and the mixture was shaken and incubated for 5 min. (step 3). Subsequently, a magnetic field was applied and the magnetic beads were drawn to the side of the vessel (step 4) and the supernatant was removed (step 5). Next, a washing solution was added and the mixture was shaken (step 6), after which the beads were again separated from the supernatant which was then again removed. This procedure was repeated once more. Subsequently, an elution solution was added (step 7) and the mixture was shaken and incubated for another 5 min. Next, the beads were separated from the supernatant which was next transferred to another vial (step 8). To this, a mixture with the internal standards of the compounds that were spiked to the serum sample was added (step 9). Details are indicated below in Table 1. Thus, no enrichment or dilution of the analytes was effected using this workflow. For comparison, the same procedure was executed with free magnetic beads 1 and without bead addition (control).

TABLE 1

| Sample | pH Adjustment | Bead | Wash | Elute | Supernatant | Dilute |
|---|---|---|---|---|---|---|
| Spiked serum* 100 μl | $K_3PO_4/K_2HPO_4$ (250 mM) 40 μl | Bead suspension (aqueous) 40 μl | water 150 μl | HCOOH (100 mM) in MeOH (70 wt.-%) 50 μl | Transfer to vial 30 μl | ISTD-Mix** 30 μl |

*serum pool from different donations to which the analytes of interest were added in a ratio of 1:40 (spike mix:serum, v/v).
**ISTD (internal standard) mix with isotopically labeled analogues of the analytes of interest as added. The ISTD allowed correction of matrix effects and inaccuracies of pipetting. Also, since these concentrations were known, this allowed for analyte recovery calculations.

3.1 Bead Assessment, Reagents and Tools

For the S/N Evaluation of analytes and comparison LPC (18:0) contents, an Agilent Infinity II multisampler and HPLC system was used in combination with an Agilent Poroshell 120 SbAq (2.1×50 mm, 2.7 μm, Serial Nr. USFAH01259) or a Thermo Fisher Hypercarb (2.1×50 mm, 3 μm, Serial Nr. 10517483) Column. As for the mobile phase water with 0.1% formic acid was used as solvent A and acetonitrile was used as solvent B. As MS/MS an AB-Sciex 6500+ TripleQuad using electronspray as ion source. For integration MultiQuant software tool was used. Data were next imported to and analyzed in JMP SAS software.

3.2 S/N Comparison for Aldosterone, Benzoylecgonine and Nortriptyline

Figure 2:
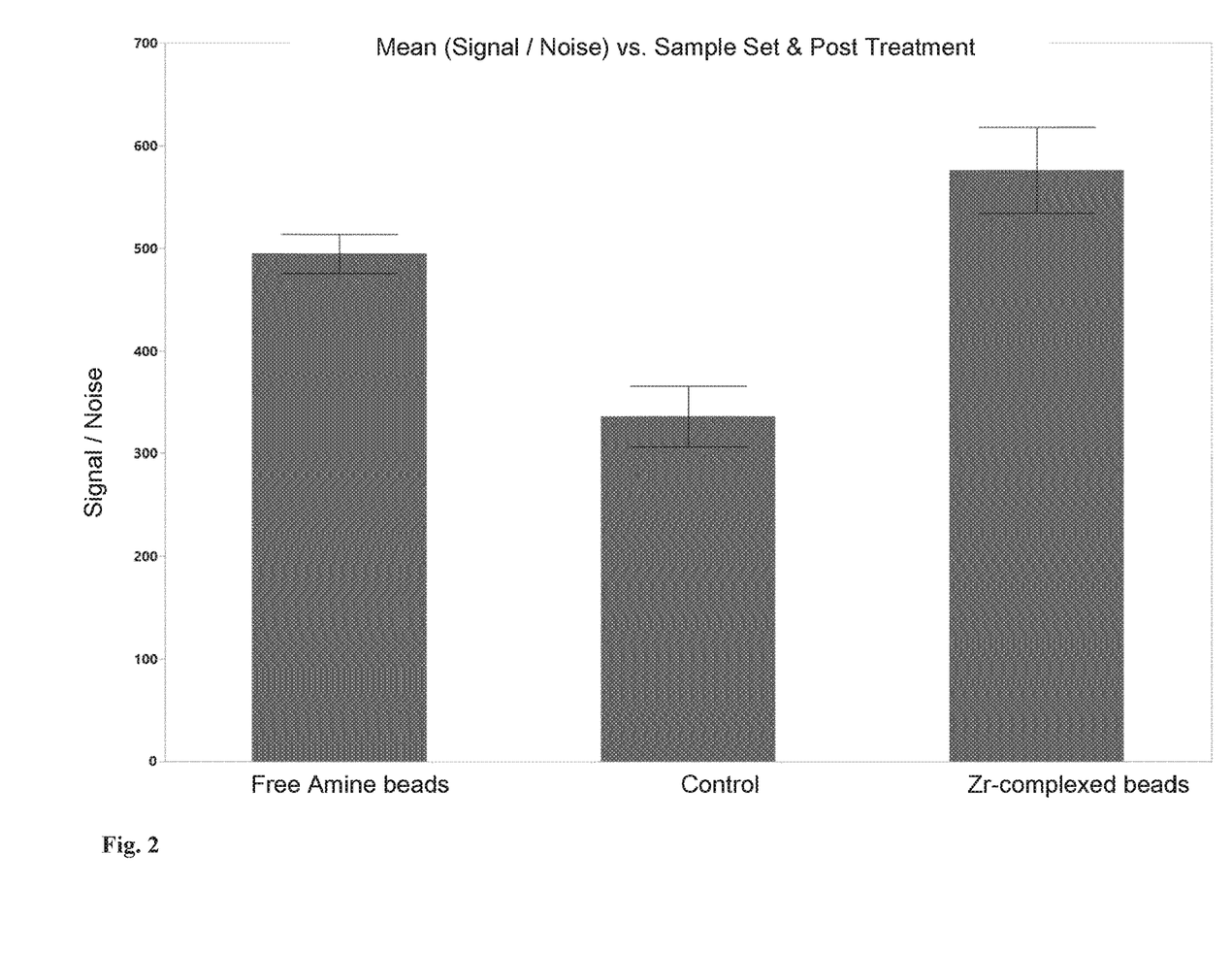
FIG. 2: shows the S/N ratio's for Aldosterone samples.
Figure 3:
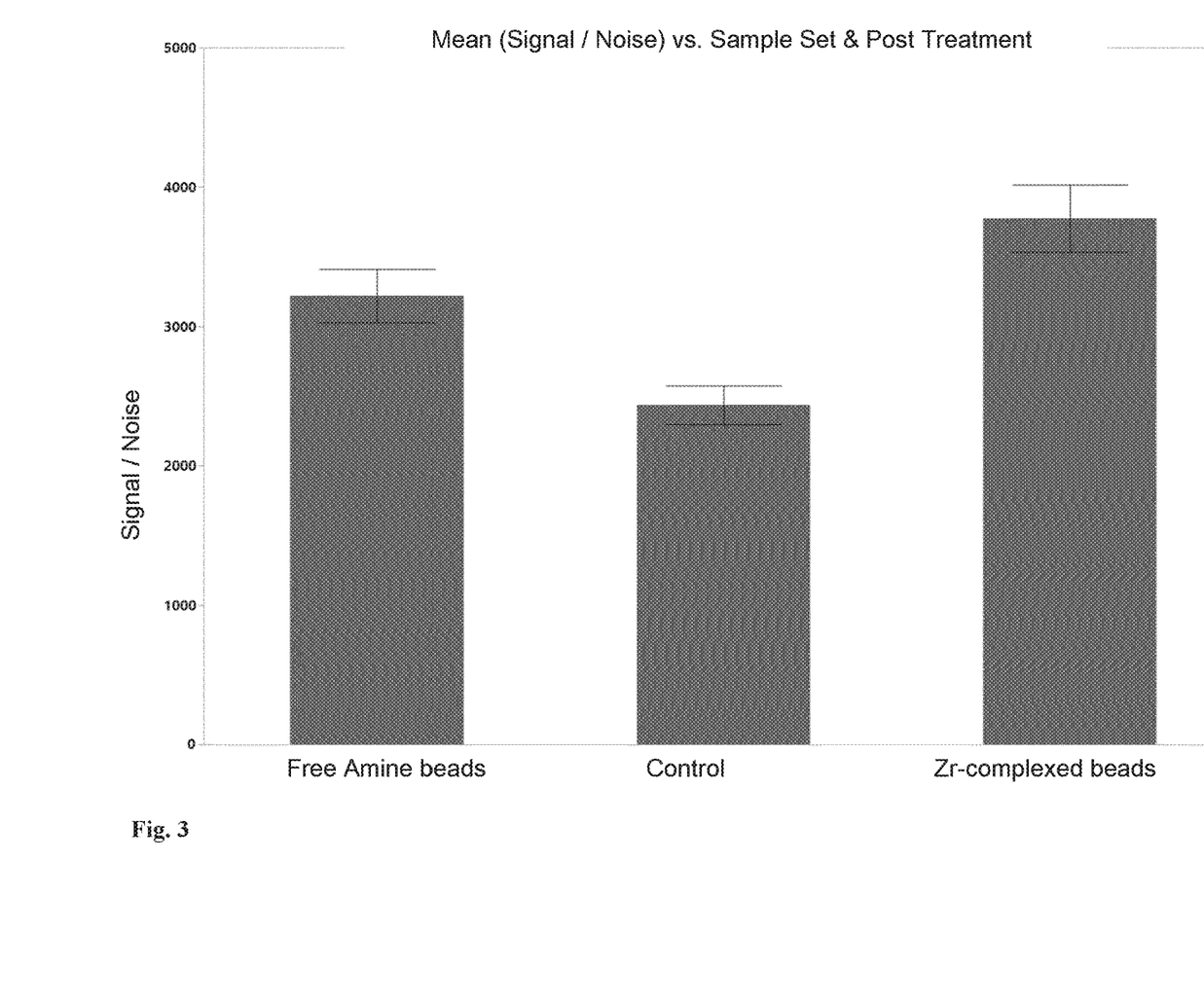
FIG. 3: shows the S/N ratio's for nortriptyline samples.
Figure 4:
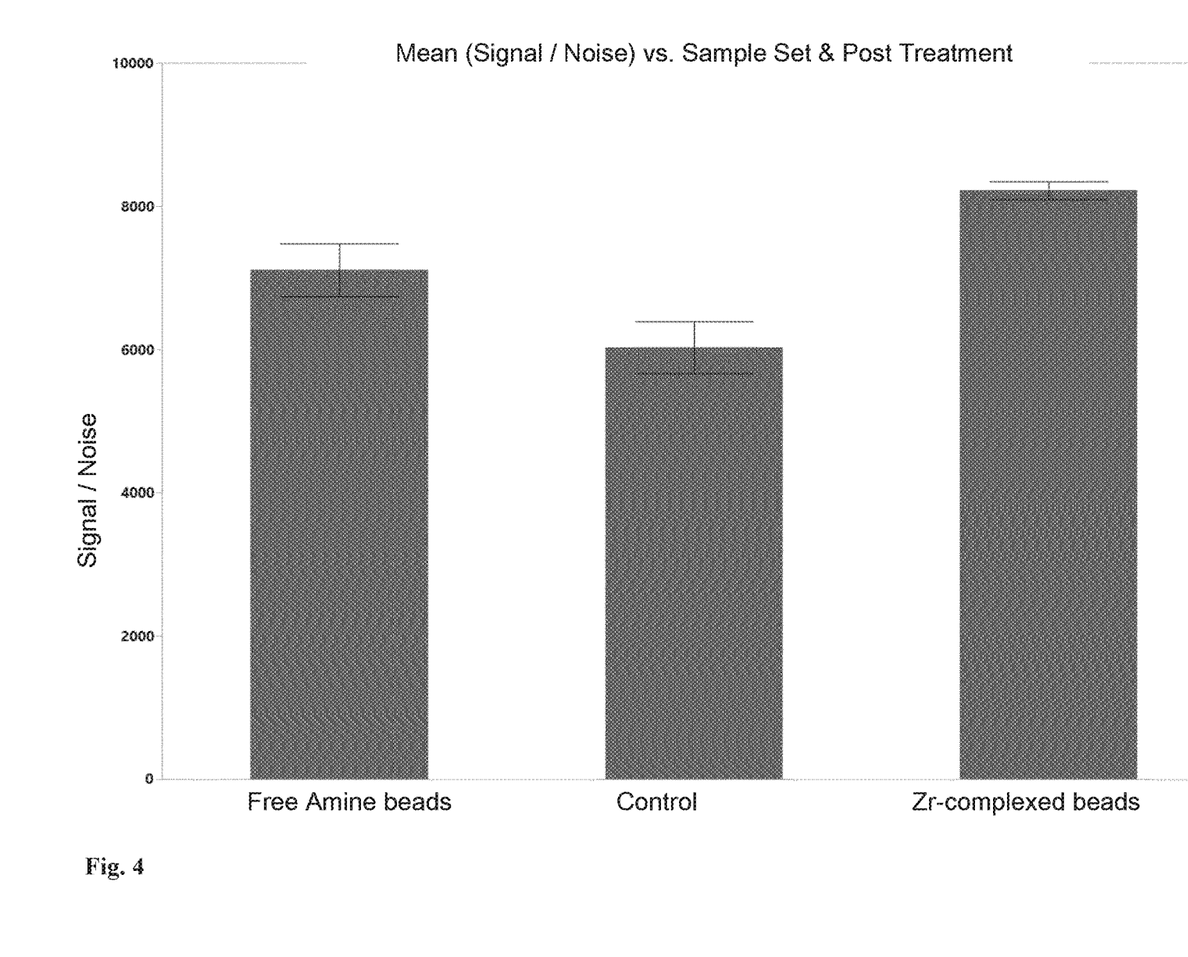
FIG. 4: shows the S/N ratio's for benzoylecgonine samples.

One criterion for bead functioning is a significant improvement of S/N (signal to noise ratio) of clinically relevant analytes. To this end S/N for the different samples were compared for aldosterone. Showing that treatment with the Zr-complexed magnetic beads from Example 2 lead to a S/N increase of factor ~2 when compared to the non-treated sample. The "free Amine bead" refers to the magnetic bead 1 having free amino groups that was used for ligand conjugation and Zr-complexation. It is observed, that this free Amine bead also yielded a sample that allows for a better S/N, however the S/N of the Zr-complexed magnetic beads from Example 2 also outcompeted this bead. The results are graphically shown in FIG. 2. Comparable results were obtained for the other analytes nortriptyline (FIG. 3) and benzoylecgonine (FIG. 4).

3.3 LPC (18:0) Comparison

Figure 5:
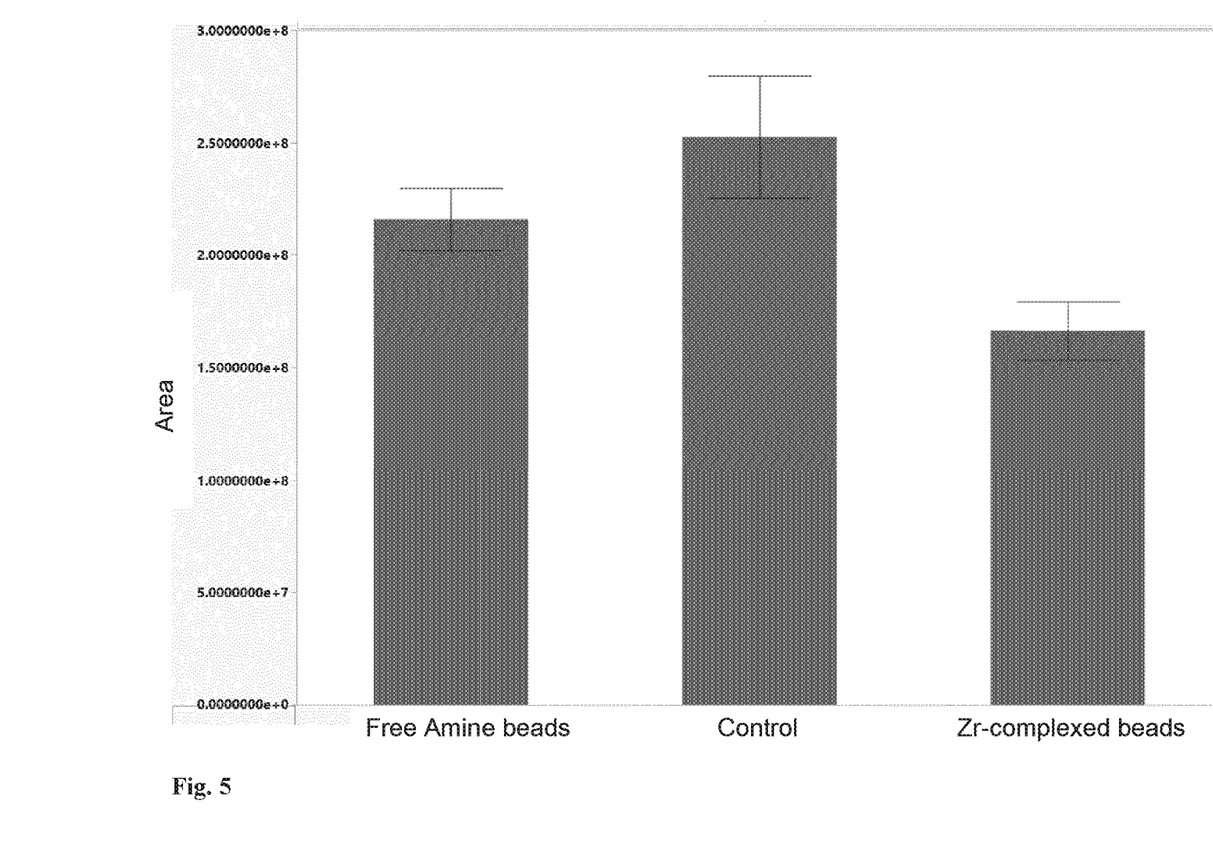
FIG. 5: shows the LPC (18:0) area for samples w/o (with or without) active LPC removal.

The results of the comparison of the lysophosphatidylcholine (18:0) (LPC (18:0)) contents are shown in FIG. 5. It could be seen that the sample treated with the Zr-complexed magnetic beads from Example 2 contained significantly less LPC (18:0).

It is apparent that a cleanup of sample material that removed matrix substances had a positive effect on S/N. This allows for a more sensitive and more accurate quantitation of analytes. It was shown that by treating the sample with the new bead type, i.e. the Zr-complexed magnetic beads, at least one phospholipid is removed.

CITED LITERATURE

Bylda C., Thiele, R., Kobold, U., Volmer, D. A., Analyst, 2014, 139, 2265-2276.
Guerard F., Lee Y. S., Tripier R., Szajek L. P., Deschamps J. R., Brechbiel M. W., Chem. Commun., 2013, 49:1002-1004.
Guérard, F., Lee, Y. S., Brechbiel, M. W., Chemistry, 2014, 20(19): 5584-5591.

The invention claimed is:

1. A complex comprising
i) a transition metal cation;
ii) a ligand comprising at least one chelating group; and
iii) a magnetic bead;
wherein the magnetic bead (iii) and the ligand (ii) are covalently bonded; and wherein the ligand (ii) has a general structure (I)

wherein:
--- is the bond to the magnetic bead (iii);
A is selected from the group consisting of a hydrogen atom, a —X—Y—$(CH_2)_m$—$CH_2$—$(CHR_3)_g$—$R^2$- group and $R^3$;
n, m are independently zero or an integer from 1 to 5;
p, q are independently an integer from 1 to 10;
X is —$CH_2$— or —NH—;
Y is —$CH_2$— or —C(=O)—;
$R^1$, $R^2$ are independently selected from the group consisting of hydroxamate group —N(O⁻)—C(=O)—R, wherein R is hydrogen or a C1 to C5 alkyl group, and partly or totally protonated forms of hydroxamate group; and

$R^3$ is a hydrogen atom or a —NHZ group, wherein Z is a —C(=O)—O—$CH_2$—$C_6H_5$ group (benzyloxycarbonyl group, Cbz) or a tert-butyloxycarbonyl group (Boc).

2. The complex according to claim 1, wherein the ligand (ii) has the general structure (Ia):

wherein
--- is the bond to the magnetic bead (iii); and
A is selected from the group consisting of a hydrogen atom, a —X—Y—$(CH_2)_m$—$CH_2$—$(CHR_3)_q$—$R^2$- group and $R^3$.

3. The complex according to claim 1, wherein the ligand (ii) has the general structure (Ia1) or (Ia2):

wherein
--- is the bond to the magnetic bead (iii); and
Z is a —C(=O)—O—$CH_2$—$C_6H_5$ group (benzyloycarbonyl group, Cbz) or tert-butyloxycarbonyl group (BOC).

4. The complex according to claim 1, wherein the transition metal cation (i) is selected from the group consisting of platinum-, ruthenium-, iridium-, scandium-, titanium-, vanadium-, chromium-, manganese-, iron-, cobalt-, nickel-, copper- and zinc-cation.

5. The complex according to claim 1, wherein the magnetic bead (iii) comprises a polymer matrix (P), at least one magnetic particle (M) and at least one —(CH₂)ᵣ—NH ___ group covalently bonded on the polymer matrix (P) surface(S), wherein ___ is the bond to the ligand (ii), and r is zero or an integer in the range of from 1 to 10; and wherein the polymer matrix (P) comprises at least one crosslinked (co-)polymer.

6. The complex according to claim 5, wherein the (co-)polymer of the polymer matrix (P) is crosslinked, wherein the crosslinked (co-)polymer of the polymer matrix (P) comprises a co-polymer obtained or obtainable by a method comprising polymerization of at least two different monomeric building blocks selected from the group consisting of styrene, functionalized styrenes, vinylbenzylchloride, divinylbenzene, vinylacetate, methylmethacrylate and acrylic acid.

7. The complex according to claim 6, wherein the (co-)polymer of the polymer matrix (P) is crosslinked, wherein the crosslinked (co-)polymer of the polymer matrix (P) is obtained or obtainable by co-polymerizing at least two different monomeric building blocks according to claim 6 in the presence of at least one monomeric building block which is a crosslinking agent, wherein the crosslinking agent is selected from the group consisting of divinylbenzene, bis(vinylphenyl) ethane, bis(vinylbenzyloxy) hexane, bis(vinylbenzyloxy) dodecane and mixtures of two or more of these crosslinking agents.

8. The complex according to claim 7, wherein the crosslinking agent at least comprises divinylbenzene.

9. The complex according to claim 5, wherein the at least one magnetic particle (M) comprises a compound selected from the group consisting of metal, metal carbide, metal nitride, metal sulfide, metal phosphide, metal oxide, metal chelate and a mixture of two or more thereof.

10. The complex according to claim 9, wherein the at least one magnetic particle (M) comprises an iron oxide selected from the group consisting of Fe₃O₄, α-Fe₂O₃, γ-Fe₂O₃, MnFeₓOᵧ, CoFeₓOᵧ, NiFeₓOᵧ, CuFeₓOᵧ, ZnFeₓOᵧ, CdFeₓOᵧ, BaFeₓO and SrFeₓO, wherein x is an integer of from 1 to 3, and wherein y is 3 or 4.

11. The complex according to claim 5, wherein the (co-)polymer of the polymer matrix (P) is crosslinked, wherein the crosslinked (co-)polymer of the polymer matrix (P) comprises a co-polymer obtained or obtainable by a method comprising polymerization of at least two different monomeric building blocks, and wherein the at least two different monomeric building blocks are selected from the group consisting of the following monomers:

-continued wherein r is zero or an integer in the range of from 1 to 10;

$R^1$, $R^2$, $R^3$, $R^4$ and $R^5$, being independently of each other selected from the group consisting of —N₃, —NH₂, —Br, —I, —F, —NR'R", —NR'R"R'", —COOH, —CN, —OH, —OR', —COOR', —NO₂, —SH₂, —SO₂, —R'(OH)x, —R'(COOH)x, —R'(COOR")x, —R' (OR")x, —R'(NH₂)x, —R'(NHR")x, —R'(NR"R'")x, —R'(Cl)x, —R'(I)x, —R'(Br)x, —R'(F)x, R'(CN)x, —R'(N₃)x, —R'(NO₂)x, —R' (SH₂)x, —R' (SO₂)x, alkyl, aryl, cycloalkyl, heteroaryl, heterocycloalkyl; with R', R" and R'" being, independently of each other, selected from the group consisting of alkyl, aryl, cycloalkyl, heteroaryl, heterocycloalkyl, halides, hydrogen, sulfides, nitrates and amines; and wherein x is an integer in the range of from 1 to 3.

12. The complex according to claim 11, wherein the (co-)polymer of the polymer matrix (P) is crosslinked, wherein the crosslinked (co-)polymer of the polymer matrix (P) is obtained or obtainable by co-polymerizing at least two different monomeric building blocks according to claim 7 in the presence of at least one monomeric building block which is a crosslinking agent, wherein the crosslinking agent is selected from the group consisting of divinylbenzene, bis(vinylphenyl)ethane, bis(vinylbenzyloxy)hexane, bis(vinylbenzyloxy)dodecane and mixtures of two or more of these crosslinking agents.

13. The complex according to claim 12, wherein the crosslinking agent at least comprises divinylbenzene.

14. The complex according to claim 1 comprising from 1 to 4 of the chelating groups.

15. A method for decreasing the content of at least one phosphor-oxy-substance in a fluid sample, comprising the steps:
 a) providing a fluid sample comprising at least one analyte of interest and at least one phosphor-oxy-substance;
 b) optionally adjusting the pH value of the fluid sample, so that the pH value of the fluid sample is in the range of from 2.5 to 12 thereby obtaining a pH adjusted fluid sample;
 c) adding at least one first complex, wherein the complex comprises:
  i) a transition metal cation;
  ii) a ligand comprising at least one chelating group; and
  iii) a magnetic bead;
  wherein the magnetic bead (iii) and the ligand (ii) are covalently bonded; thereby forming a suspension comprising a second complex, which comprises the first complex and the at least one phosphor-oxy-substance in complexed form;
 d) spacely separating the second complex in the suspension obtained in (c) by application of a magnetic field, thereby obtaining a supernatant substantially free of the second complex;

e) removing the supernatant, thereby obtaining a separated second complex;

wherein the ligand (ii) has a general structure (I)

wherein:

--- is the bond to the magnetic bead (iii);

A is selected from the group consisting of a hydrogen atom, a —X—Y—(CH$_2$)$_m$—CH$_2$—(CHR$_3$)$_g$—R$^2$- group and R$^3$;

n, m are independently zero or an integer from 1 to 5;

p, q are independently an integer from 1 to 10;

X is —CH$_2$— or —NH—;

Y is —CH$_2$— or —C(=O)—;

R$^1$, R$^2$ are independently selected from the group consisting of hydroxamate group —N(O$^-$)—C(=O)—R, wherein R is hydrogen or a C1 to C5 alkyl group, and partly or totally protonated forms of hydroxamate group; and R$^3$ is a hydrogen atom or a —NHZ group, wherein Z is a —C(=O)—O—CH$_2$—C$_6$H$_5$ group (benzyloxycarbonyl group, Cbz) or a tert-butyloxycarbonyl group Boc).

16. A supernatant obtained or obtainable from the method of claim 15.

17. A method for qualitative and/or quantitative determination of at least one analyte in a fluid sample, comprising the steps of the purification method according to claim 15 and further comprising a step of qualitative and/or quantitative determination of the at least one analyte in the supernatant obtained from (e) and/or (f) and/or (g).

18. A method for determining the kind and/or amount of at least one phosphor-oxy-substance in a fluid sample, comprising the steps of the purification method according to claim 15 and further comprising:

h) adding an aqueous and/or organic elution solution to the (further) separated second complex obtained according to (e) and/or (f), wherein the aqueous and/or organic elution solution contains a buffer and/or a reductant, and/or wherein the adding is done in a reductive atmosphere, thereby separating the at least one phosphor-oxy-substance from the separated second complex and obtaining a solution comprising the at least one phosphor-oxy-substance;

j) determining the kind and/or amount of the at least one phosphor-oxy-substance in the solution obtained according to (h).

* * * * *